United States Patent [19]
Kelley

[11] Patent Number: 5,325,965
[45] Date of Patent: Jul. 5, 1994

[54] CONTAMINATED NEEDLE DISPOSAL SYSTEM AND DEVICE

[76] Inventor: James H. Kelley, 17159 E. Evans Ave., Aurora, Colo. 80013

[21] Appl. No.: 99,518

[22] Filed: Jul. 30, 1993

[51] Int. Cl.$^5$ ............................................. B65D 83/10
[52] U.S. Cl. ................................. 206/366; 206/370; 206/820; 604/110; 604/192
[58] Field of Search ............... 604/110, 192, 198, 263; 206/363–367, 370, 820; 232/43.1

[56] References Cited

U.S. PATENT DOCUMENTS

| | | | |
|---|---|---|---|
| 5,190,169 | 3/1993 | Sincock | 211/60.1 |
| 5,209,733 | 5/1993 | Lever et al. | 604/110 |
| 5,230,426 | 7/1993 | Keefe et al. | 206/205 |
| 5,230,428 | 7/1993 | McShane | 206/363 |

*Primary Examiner*—C. Fred Rosenbaum
*Assistant Examiner*—Corrine Maglione
*Attorney, Agent, or Firm*—Leon Gilden

[57] ABSTRACT

First and second containers arranged for securement relative to one another about a hinge for the storage of first and second matrix of disposal cylinders is provided, wherein each cylinder includes a frangible interconnection between an adjacent cylinder of an adjacent matrix, wherein each cylinder includes a fluid impermeable rigid side wall and floor having a polymeric top wall arranged to receive and secure a syringe needle therewithin to secure the syringe and needle and permit disposal of individual of said cylinders along with the associated syringe to provide destruction of frangible interconnection between adjacent cylinders.

3 Claims, 3 Drawing Sheets

CONTAMINATED NEEDLE DISPOSAL SYSTEM AND DEVICE

BACKGROUND OF THE INVENTION

1. Field of the Invention

The field of invention relates to syringe and needle disposal structure, and more particularly pertains to a new and improved syringe needle disposal apparatus wherein the same is directed to the sanitary and safe disposal of syringe needles.

2. Description of the Prior Art

The advent of communicable and contagious diseases, particularly such as AIDS, in use and transmission of such diseases by syringes requires the safe disposal of such needles.

The instant invention attempts to overcome deficiencies of the prior art by permitting the storage of matrix of disposable cylinders, with each cylinder having a bactericide and associated frangible interconnection relative to adjacent cylinders to permit the removal of individual cylinders for their subsequent disposal and in this respect, the present invention substantially fulfills this need.

SUMMARY OF THE INVENTION

In view of the foregoing disadvantages inherent in the known types of syringe needle disposal apparatus now present in the prior art, the present invention provides a syringe needle disposal apparatus wherein the same is directed to the disposal of individual cylinders or matrix of cylinders mounted within an associated container structure. As such, the general purpose of the present invention, which will be described subsequently in greater detail, is to provide a new and improved syringe needle disposal apparatus which has all the advantages of the prior art syringe needle disposal apparatus and none of the disadvantages.

To attain this, the present invention provides first and second containers arranged for securement relative to one another about a hinge for the storage of first and second matrix of disposal cylinders, wherein each cylinder includes a frangible interconnection between an adjacent cylinder of an adjacent matrix, wherein each cylinder includes a fluid impermeable rigid side wall and floor having a polymeric top wall arranged to receive and secure a syringe needle therewithin to secure the syringe and needle and permit disposal of individual of said cylinders along with the associated syringe to provide destruction of frangible interconnection between adjacent cylinders.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved syringe needle disposal apparatus which has all the advantages of the prior art syringe needle disposal apparatus and none of the disadvantages.

It is another object of the present invention to provide a new and improved syringe needle disposal apparatus which may be easily and efficiently manufactured and marketed.

It is a further object of the present invention to provide a new and improved syringe needle disposal apparatus which is of a durable and reliable construction.

An even further object of the present invention is to provide a new and improved syringe needle disposal apparatus which is susceptible of a low cost of manufacture with regard to both materials and labor, and which accordingly is then susceptible of low prices of sale to the consuming public, thereby making such syringe needle disposal apparatus economically available to the buying public.

Still yet another object of the present invention is to provide a new and improved syringe needle disposal apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
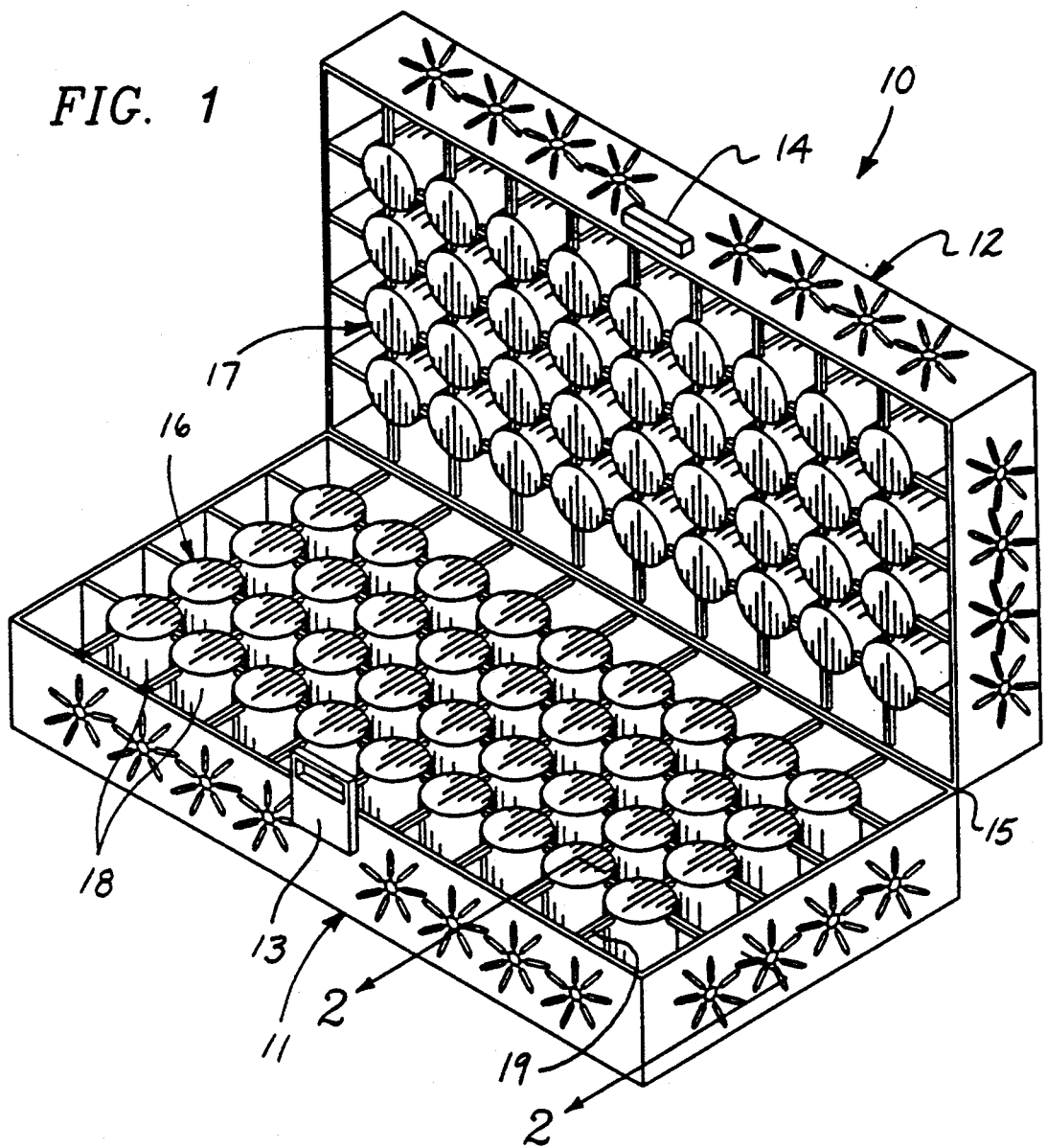
FIG. 1 is an isometric illustration of the invention.
Figure 2:
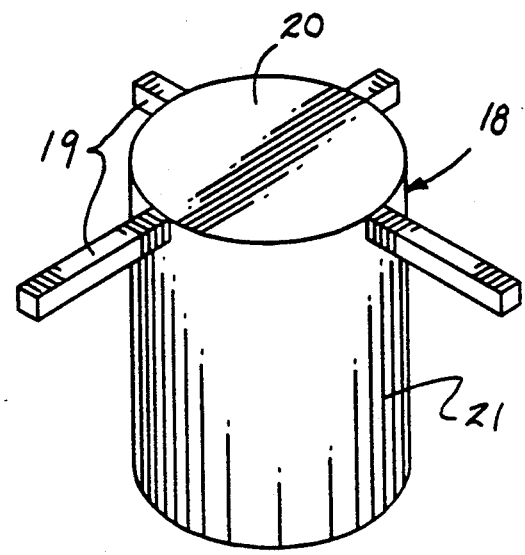
FIG. 2 is an isometric illustration of an individual disposable cylinder structure of the invention.
Figure 3:
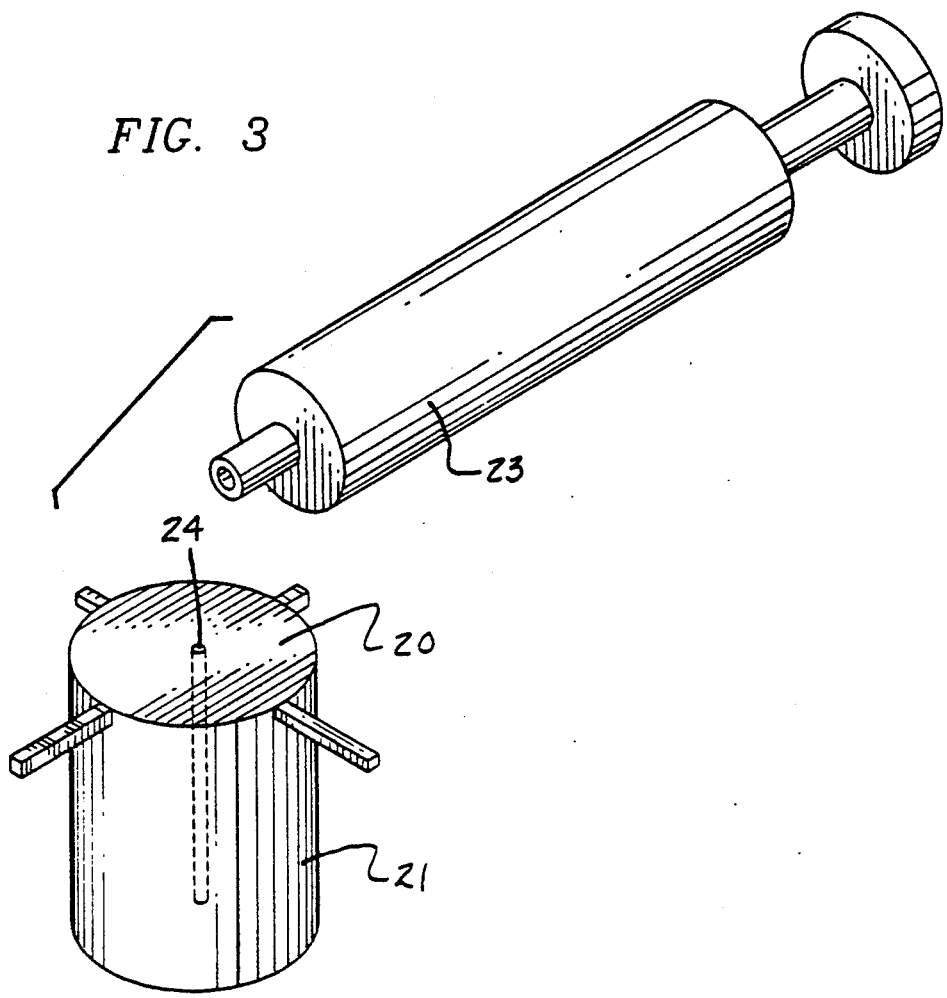
FIG. 3 is an isometric illustration of a syringe needle directed into an individual cylinder.
Figure 4:
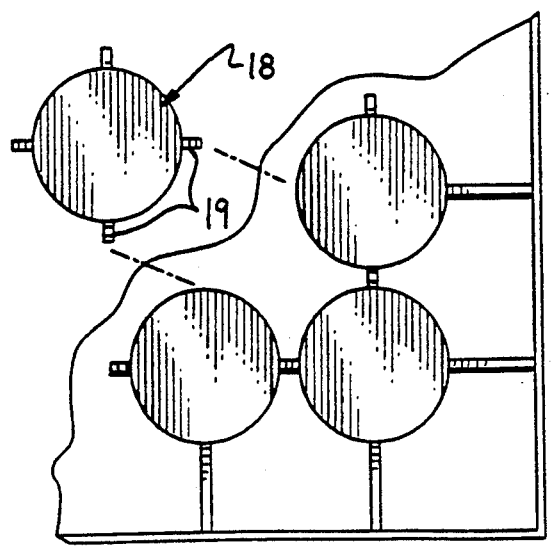
FIG. 4 is an orthographic top view indicating the removal of an individual cylinder from a matrix of said cylinders.
Figure 5:
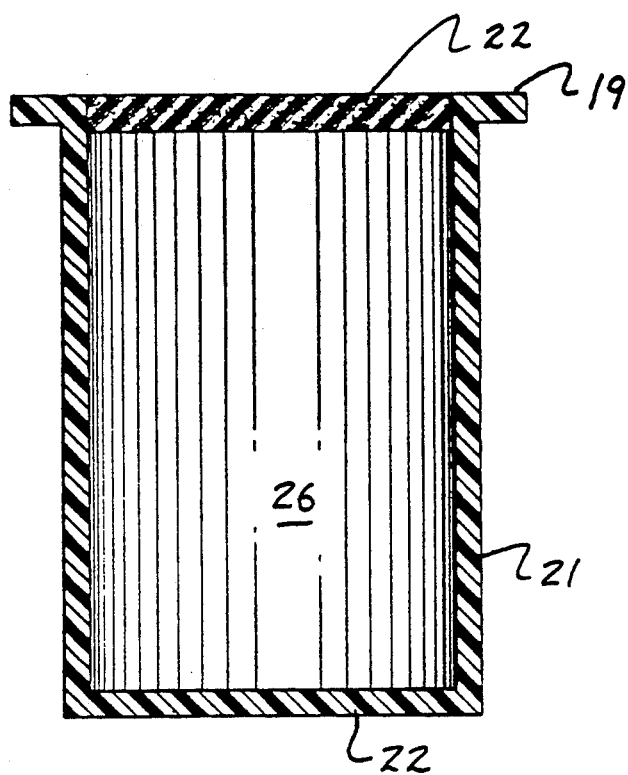
FIG. 5 is an orthographic cross-sectional illustration of the individual cylinder structure.

With reference now to the drawings, and in particular to FIGS. 1 to 6 thereof, a new and improved syringe needle disposal apparatus embodying the principles and concepts of the present invention and generally designated by the reference numeral 10 will be described.

Figure 6:
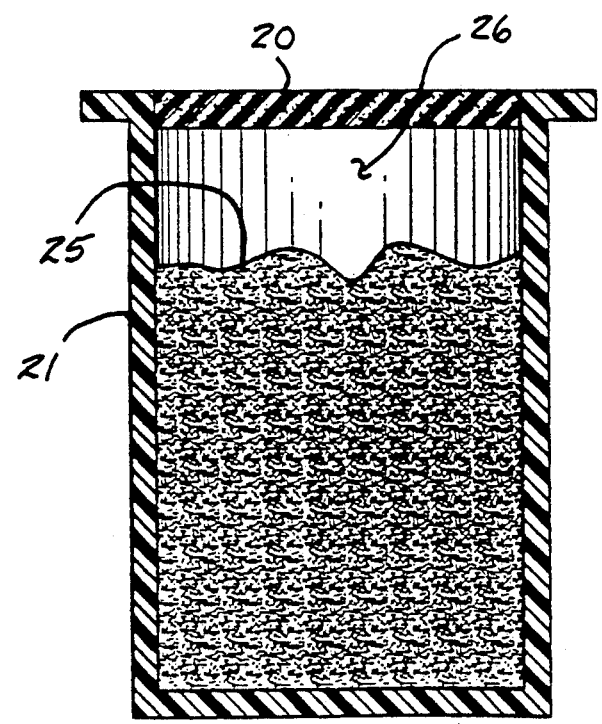
FIG. 6 is an orthographic cross-sectional illustration of an individual cylinder having a bactericide impregnated sponge member contained therewithin.

More specifically, the syringe needle disposal apparatus 10 of the instant invention provides a first container 11 mounted to a second container 12 about a hinge web 15 interconnecting a respective first and second container rear side wall, with the respective first and second container forward side wall including respective first and second latches 13 and 14 arranged for securement of the first and second containers 11 and 12 together in a stored configuration. A first matrix of disposable cylinders 16 is mounted within the first container, with a second matrix of disposable cylinders 17 mounted within the second container. The individual containers of the first and second matrix of containers 16 and 17 are comprised of disposable cylinders 18, with each disposable cylinder including a radial array of frangible mounting rods 19 extending radially from each of the container side walls 21 interconnecting adjacent side walls of adjacent cylinders 18. A cylinder top wall 20 is formed typically of polymeric styrofoam, while the side wall 21 and the floor 22 is formed of a rigid fluid impermeable polymeric material. In this manner, a syringe 23 directs a syringe needle 24 through the styrofoam top wall 20 permitting securement and breakage of the needle within the housing cavity 26 of the individual container cylinder. The container structure, as indicated in FIG. 6, is arranged to further include a bactericide impregnated sponge 25 positioned within the housing cavity 26 in adjacency to the top wall 20 to further render harmless a syringe needle directed into the associated cylinder 18.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A contaminated needle disposal system/device, comprising, a first container and a second container, with the first container having a first container rear wall, the second container having a second container rear wall, wherein the first container rear wall and the second container rear wall include an interconnecting hinge, with the first container including a first matrix of disposable cylinders contained therewithin, and the second container having a matrix of second cylinders contained therewithin, said cylinders of said first matrix of cylinders and said second matrix of cylinders each include a radial array of frangible mounting rods extending therefrom interconnecting adjacent cylinders.

2. An apparatus as set forth in claim 1 wherein each of said cylinders includes a rigid fluid impermeable side wall and rigid fluid impermeable floor, and a styrofoam top wall defining a housing cavity between the floor and top wall.

3. An apparatus as set forth in claim 2 wherein the housing cavity includes a bactericide impregnated sponge member positioned within the cavity in adjacency to the top wall.

* * * * *